(12) United States Patent
Hull et al.

(10) Patent No.: US 8,408,480 B2
(45) Date of Patent: Apr. 2, 2013

(54) SELF-CLEANING SPRAY TIP

(75) Inventors: Les Hull, Attleboro, MA (US); Derek Rissman, Waltham, MA (US); Jason Fortier, Concord, MA (US); Art Driscoll, Reading, MA (US)

(73) Assignee: Confluent Surgical, Inc., Bedford, MA (US)

( * ) Notice: Subject to any disclaimer, the term of this patent is extended or adjusted under 35 U.S.C. 154(b) by 2 days.

(21) Appl. No.: 12/580,307

(22) Filed: Oct. 16, 2009

(65) Prior Publication Data
US 2010/0096481 A1 Apr. 22, 2010

Related U.S. Application Data

(63) Continuation-in-part of application No. 12/427,965, filed on Apr. 22, 2009.

(60) Provisional application No. 61/047,826, filed on Apr. 25, 2008.

(51) Int. Cl.
*B05B 15/02* (2006.01)

(52) U.S. Cl. ........ 239/107; 239/104; 239/106; 239/399; 239/433; 239/437; 239/490; 239/491; 239/533.13; 239/602; 239/DIG. 12

(58) Field of Classification Search .................. 239/104, 239/106, 107, 433, 437, 533.1, 533.13, 533.14, 239/597, 599, 602, DIG. 12, 399, 490, 491
See application file for complete search history.

(56) References Cited

U.S. PATENT DOCUMENTS

| | | | |
|---|---|---|---|
| 2,402,741 A * | 6/1946 | Draviner | 239/602 |
| 3,214,102 A * | 10/1965 | Meyer | 239/107 |
| 3,237,866 A * | 3/1966 | Lovell | 239/533.14 |
| 3,286,931 A * | 11/1966 | Webb | 239/533.13 |
| 3,828,980 A | 8/1974 | Creighton et al. | |
| 4,040,420 A | 8/1977 | Speer | |
| 4,359,049 A | 11/1982 | Redl et al. | |
| 4,538,920 A | 9/1985 | Drake | |
| 4,631,055 A | 12/1986 | Redl et al. | |
| 4,735,616 A | 4/1988 | Eibl et al. | |
| 4,753,536 A | 6/1988 | Spehar et al. | |
| 4,767,026 A | 8/1988 | Keller et al. | |
| 4,842,581 A | 6/1989 | Davis | |
| 4,872,368 A | 10/1989 | Miller et al. | |
| 4,978,336 A | 12/1990 | Capozzi et al. | |
| 4,979,942 A | 12/1990 | Wolf et al. | |
| 5,049,135 A | 9/1991 | Davis | |
| 5,104,375 A | 4/1992 | Wolf et al. | |
| 5,115,978 A * | 5/1992 | King et al. | 239/107 |
| 5,116,315 A | 5/1992 | Capozzi et al. | |
| 5,249,709 A | 10/1993 | Duckworth et al. | |
| 5,249,862 A | 10/1993 | Herold et al. | |
| 5,328,462 A | 7/1994 | Fischer | |
| 5,333,760 A | 8/1994 | Simmen | |
| 5,413,253 A | 5/1995 | Simmen | |
| 5,445,614 A | 8/1995 | Haber et al. | |
| 5,474,540 A | 12/1995 | Miller et al. | |
| 5,605,255 A | 2/1997 | Reidel et al. | |
| 5,643,206 A | 7/1997 | Fischer | |
| 5,665,066 A | 9/1997 | Fischer | |
| 5,740,965 A | 4/1998 | Miyagi et al. | |
| 5,810,885 A | 9/1998 | Zinger | |
| 5,819,988 A | 10/1998 | Sawhney et al. | |
| 5,890,655 A * | 4/1999 | Collias et al. | 239/107 |
| RE36,235 E | 6/1999 | Keller et al. | |

(Continued)

*Primary Examiner* — Steven J Ganey

(57) ABSTRACT

A spray tip assembly capable of self-clearing is provided. The spray tip assembly includes a distal end including an outlet. The outlet defines at least a first configuration during a first condition and at least a second configuration during a second condition. The distal end may be configured to at least one of flex and expand such that the outlet changes from the first configuration to the second configuration.

17 Claims, 10 Drawing Sheets

U.S. PATENT DOCUMENTS

| | | | |
|---|---|---|---|
| 5,941,462 A * | 8/1999 | Sandor | 239/602 |
| 6,047,861 A | 4/2000 | Vidal et al. | |
| 6,065,645 A | 5/2000 | Sawhney et al. | |
| 6,132,396 A | 10/2000 | Antanavich et al. | |
| 6,161,730 A | 12/2000 | Heusser et al. | |
| 6,398,761 B1 | 6/2002 | Bills et al. | |
| 6,527,749 B1 | 3/2003 | Roby et al. | |
| 6,585,696 B2 | 7/2003 | Petersen et al. | |
| 6,609,666 B1 * | 8/2003 | Blake | 239/533.13 |
| 6,648,852 B2 | 11/2003 | Wirt et al. | |
| 6,698,622 B2 | 3/2004 | Sawhney et al. | |
| 6,752,292 B2 | 6/2004 | Van Herpen | |
| 6,769,574 B1 | 8/2004 | Keller | |
| 6,773,414 B2 | 8/2004 | Ljungquist | |
| 6,783,514 B2 | 8/2004 | Tovey et al. | |
| 6,820,766 B2 | 11/2004 | Keller et al. | |
| 6,835,186 B1 | 12/2004 | Pennington et al. | |
| 6,852,099 B2 | 2/2005 | Redl et al. | |
| 6,884,232 B1 | 4/2005 | Hagmann et al. | |
| 6,921,381 B2 | 7/2005 | Spero et al. | |
| 6,994,686 B2 | 2/2006 | Cruise et al. | |
| 7,124,574 B2 | 10/2006 | Horn et al. | |
| 7,124,914 B2 | 10/2006 | Foster et al. | |
| 7,128,278 B2 | 10/2006 | Archambeau et al. | |
| 7,131,597 B2 | 11/2006 | Scattergood | |
| 7,140,558 B2 | 11/2006 | McCracken et al. | |
| 7,140,560 B2 | 11/2006 | Stotts et al. | |
| 7,140,797 B2 | 11/2006 | Hunter et al. | |
| 7,152,396 B2 | 12/2006 | Cheng | |
| 7,152,813 B2 | 12/2006 | Chen | |
| 7,156,835 B2 | 1/2007 | Epstein | |
| 7,159,796 B2 | 1/2007 | Yquel | |
| 7,164,133 B2 | 1/2007 | Hjertman et al. | |
| 7,173,733 B2 | 2/2007 | Gauthier et al. | |
| 7,178,742 B2 | 2/2007 | Mellentine et al. | |
| 7,178,743 B2 | 2/2007 | Clarke, III et al. | |
| 7,178,744 B2 | 2/2007 | Tapphorn et al. | |
| 7,182,279 B2 | 2/2007 | Wang | |
| 7,185,829 B2 | 3/2007 | Sundholm | |
| 7,191,917 B2 | 3/2007 | Brinz et al. | |
| 7,191,959 B2 | 3/2007 | Kutay et al. | |
| 7,195,135 B1 | 3/2007 | Garcia et al. | |
| 7,195,180 B2 | 3/2007 | Lee | |
| 7,201,336 B2 | 4/2007 | Blelle et al. | |
| 7,207,969 B2 | 4/2007 | Epstein et al. | |
| 7,217,254 B2 | 5/2007 | Kirwan et al. | |
| 7,222,752 B2 | 5/2007 | Ponton | |
| 7,223,426 B2 | 5/2007 | Cheng et al. | |
| 7,225,999 B2 | 6/2007 | Foianini et al. | |
| 7,232,080 B2 | 6/2007 | Kutay et al. | |
| 7,232,082 B2 | 6/2007 | Muhlhausen et al. | |
| 7,237,693 B2 | 7/2007 | Brennan et al. | |
| 7,237,726 B2 | 7/2007 | Yu | |
| 7,244,248 B2 | 7/2007 | Azzolini | |
| 7,246,758 B2 | 7/2007 | Wang | |
| 7,252,243 B2 | 8/2007 | Bjorn et al. | |
| 7,252,247 B2 | 8/2007 | Holm et al. | |
| 7,264,179 B2 | 9/2007 | Robbins | |
| 7,267,288 B2 | 9/2007 | Wheeler, Jr. et al. | |
| 7,270,654 B2 | 9/2007 | Griego et al. | |
| 7,275,699 B2 | 10/2007 | Schmidt | |
| 7,278,985 B2 | 10/2007 | Agerup | |
| 2002/0104851 A1 | 8/2002 | Parise | |
| 2002/0165483 A1 | 11/2002 | Miller et al. | |
| 2003/0062426 A1 * | 4/2003 | Gregory et al. | 239/107 |
| 2003/0183653 A1 | 10/2003 | Bills | |
| 2003/0209612 A1 | 11/2003 | Hahnen | |

* cited by examiner

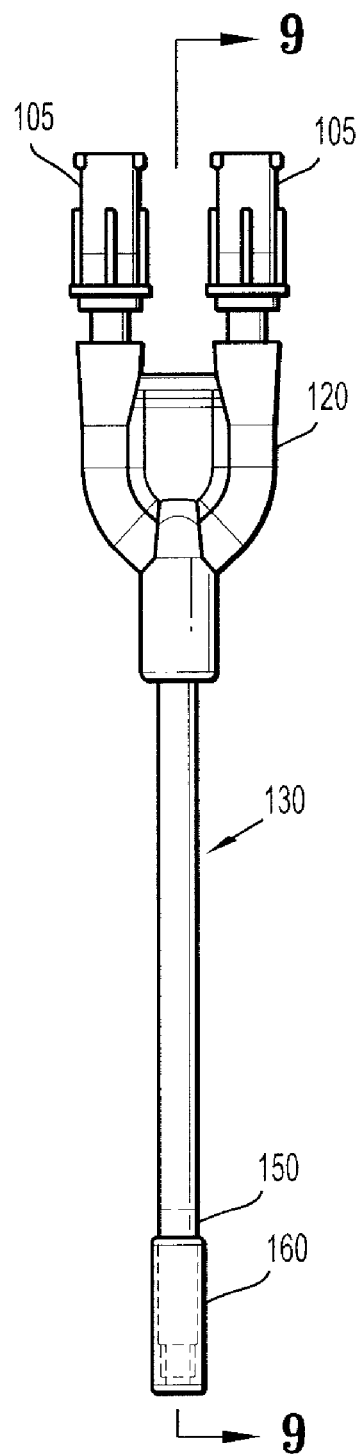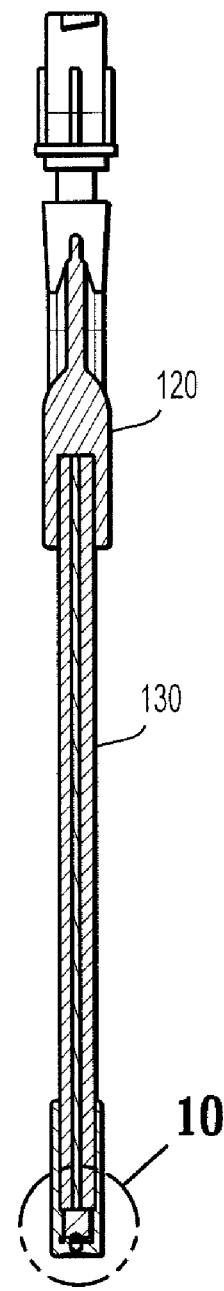
FIG. 8  FIG. 9

SELF-CLEANING SPRAY TIP

CROSS-REFERENCE TO RELATED APPLICATION

The present application is a continuation-in-part of U.S. patent application Ser. No. 12/427,965, filed Apr. 22, 2009, which claims the benefit of and priority to U.S. Provisional Application Ser. No. 61/047,826, filed on Apr. 25, 2008, the entire content of each application being incorporated by reference herein.

BACKGROUND

1. Technical Field

The present disclosure relates to assemblies for mixing and applying two or more components. More particularly, the present disclosure relates to a spray tip for use with an applicator assembly, wherein the spray tip is capable self-clearing.

2. Background of Related Art

Applicator assemblies for dispensing two or more components are known. In the medical device field, such assemblies are typically used for applying bioadhesives, polymers and other synthetic material used in wound closure. Because of the reactant nature of the components used to foul the bioadhesive, mixing of the components does not occur until the solution is ready to be applied. Mixing of the components too soon before application may result in premature hardening of the mixture, thereby making application of the solution impossible. Thus, in known applicator assemblies, the two or more components are maintained separately until just prior to application. The applicator assemblies include one or more mixing means for mixing the two or more solutions prior to application. The mixing means may be passive, i.e., spiral configuration in the tubing, or instead may be active, i.e., mixing blade or impeller. Once mixed, the solution may be applied through a needle-like output or may instead be ejected through a spray assembly. Thorough mixing of the two or more components prior to application is important to ensure that the solution will perform as intended.

Intermittent use of an applicator assembly, as may be required during a procedure, tends to clog the outlet of the applicator tip. As a result, most applicator assemblies are provided with a number of replacement tips for when clogging of the tip occurs. Replacing clogged applicator tips interrupts the flow of a procedure, is time consuming and is an added expense.

Therefore, it would be beneficial to have an applicator tip that is capable of self-clearing.

SUMMARY

Accordingly, provided is a spray tip assembly capable of self-clearing. The spray tip assembly includes a distal end including an outlet. The outlet defines at least a first configuration during a first condition and at least a second configuration during a second condition. The distal end may be configured to at least one of flex and expand such that the outlet changes from the first configuration to the second configuration. The spray tip assembly may further include a proximal end configured for operable engagement with a dispensing assembly. The distal end is composed of a material that permits at least one of flexion and expansion. At least a portion of the distal end may include silicone. The outlet defines the first configuration during normal operation and the second configuration when the outlet is obstructed. The distal end may flex and expand radially to change from the first configuration to the second configuration. The distal end may at least one of flex and expand distally outward to change from the first configuration to the second configuration. The distal end may at least one of flex and expand both radially and distally to change from the first configuration to the second configuration. The outlet may define a substantially circular opening having a first diameter in the first configuration and a second diameter in the second configuration. The outlet may define an opening have a first diameter in the first configuration and a larger diameter in the second configuration.

Also provided are self-clearing applicators. One embodiment of a self-clearing applicator includes a spray tip assembly having a distal end including an outlet. The outlet defines at least a first configuration during normal operation and at least a second configuration when the outlet is at least partially obstructed.

In another embodiment, the self-clearing applicator includes a spray tip assembly having a distal end including an outlet, the outlet defining at least a first configuration during normal operation and at least a second configuration when the outlet is at least partially obstructed.

In yet another embodiment, the self-clearing applicator includes a spray tip assembly including an outlet. The spray tip assembly is capable of clearing an obstruction from the outlet.

In still another embodiment, the self-clearing applicator includes a spray tip assembly defining an outlet. The spray tip assembly is capable of undergoing a change in cross-sectional geometry to clear an obstruction from the outlet.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 8 is a top plan view of the applicator assembly of FIG. 7;

FIG. 9 is a cross-sectional side view of the applicator assembly of FIGS. 7 and 8, taken along line 9-9 of FIG. 8;

DETAILED DESCRIPTION

Figure 1:
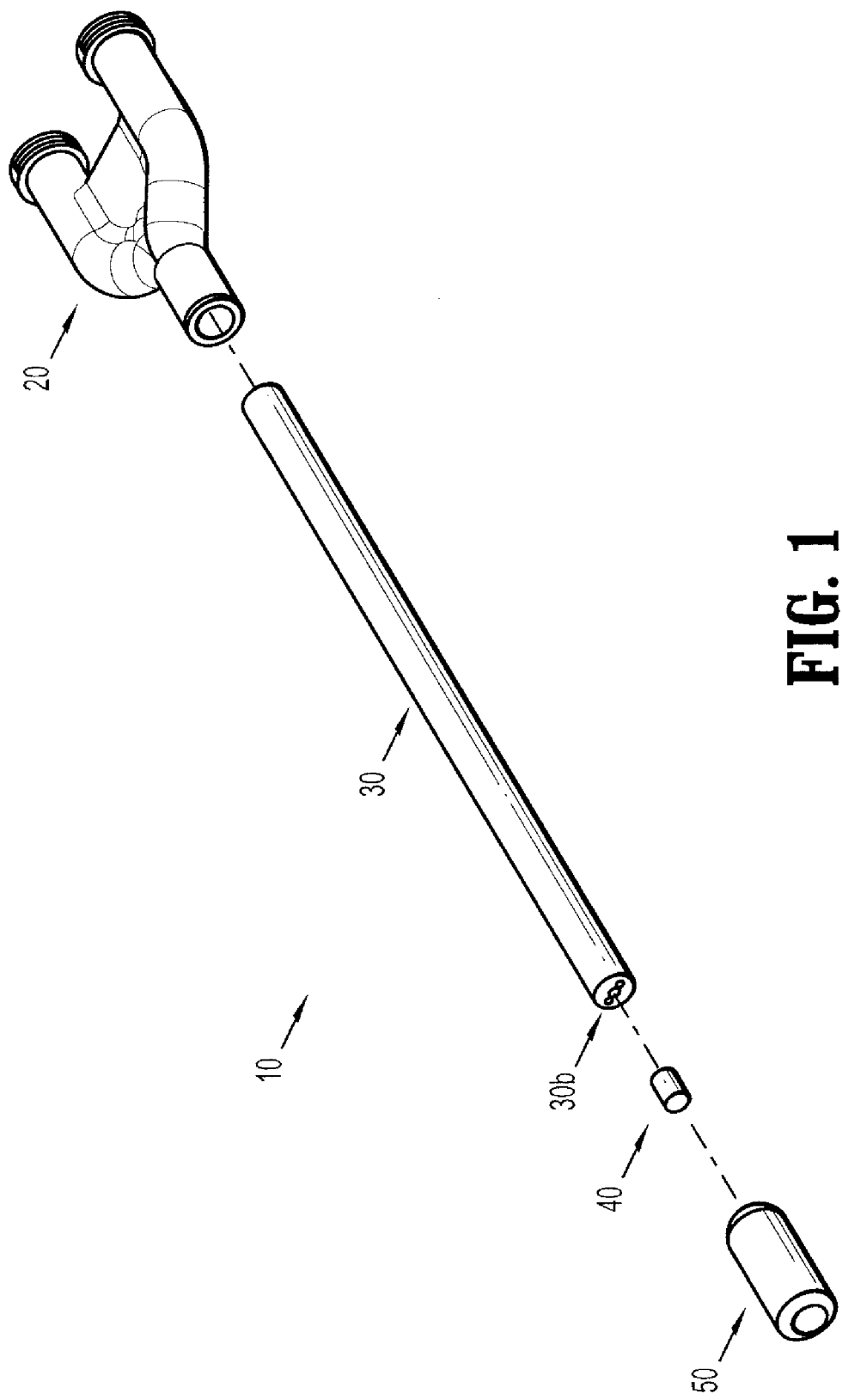
FIG. 1 is an exploded perspective view of an applicator assembly including a spray tip assembly according to an embodiment of the present disclosure.

Referring initially to FIG. 1, an applicator assembly including a spray tip assembly according the present disclosure is shown generally as applicator assembly 10. Applicator assembly 10 includes a manifold or base 20, an elongated shaft 30 extending from manifold 20, and a spray tip assembly 50 positioned on a distal end 30b of elongated shaft 30. Applicator assembly 10 further includes an insert 40 configured to be received within spray tip assembly 50 and located distal of elongated shaft 30.

Figure 2:
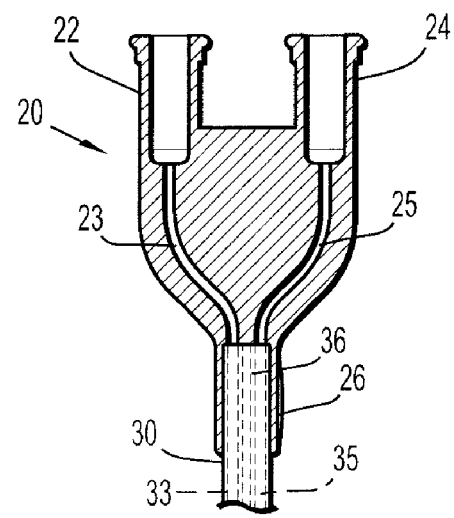
FIG. 2 is a cross-sectional side view of a manifold of the applicator assembly of FIG. 1.

With reference now to FIG. 2, manifold 20 includes a substantially Y-shaped member having a first and a second proximal extension 22, 24 and a distal extension 26. Proximal extensions 22, 24 are configured for operable engagement with a first and a second source of component (not show), e.g., syringe. Distal extension 26 is configured for operable engagement with elongated shaft 30, as will be discussed in further detail below. Manifold 20 further includes first and second component channels 23, 25. First and second component channels 23, 25 fluidly communicate the first and second sources of components with a first and a second lumen 33, 35 formed in elongated shaft 30. While manifold 20, as shown, is configured to receive only two sources of component, it is envisioned that manifold 20 may be configured to receive more than two sources of component.

Referring back to FIG. 1, elongated shaft 30 may define a substantially solid body of silicone, plastic, polymer or other flexible material. As noted above, elongated shaft 30 includes first and second component lumens 33, 35 extending the length thereof. A wire 36 composed of a malleable material also extends the length of elongated shaft 30. Wire 36 is configured to maintain elongated shaft 30 in a bent or flexed configuration after elongated shaft 30 has been bent or flexed to accommodate a given procedure. Elongated shaft 30 is secured to distal extension 26 of manifold 20 such that first and second component lumens 33, 35 align with first and second component channels 23, 25, respectively. Alternatively, elongated shaft 30 may be integrally formed at a distal end of manifold 20. Elongated shaft 30 may further include grooves, detents, threads or otherwise be configured for secure engagement with spray tip assembly 50.

Figure 3:
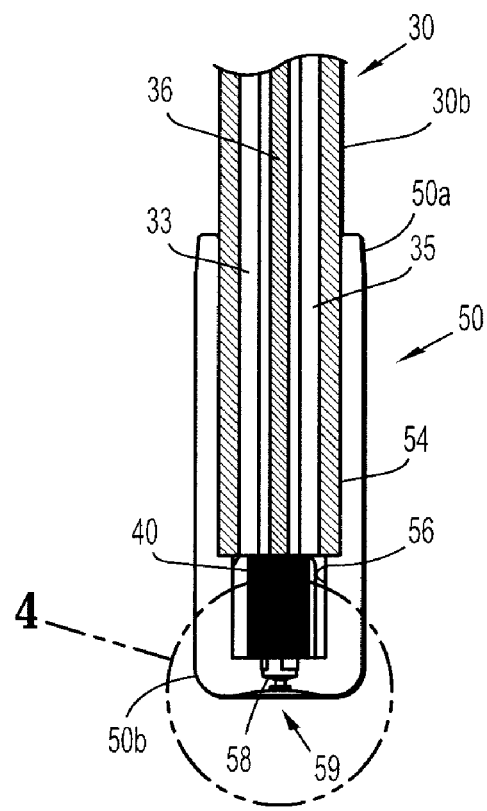
FIG. 3 is a cross-sectional side view of the spray tip assembly of the applicator assembly of FIG. 1.

With reference now to FIGS. 3-6, spray tip assembly 50 defines a substantially cylindrical body 52 having an open proximal end 52a and a substantially closed distal end 52b. Open proximal end 52a is configured to receive distal end 30b of elongated shaft 30 (FIG. 3). As will be discussed in further detail below, distal end 52b includes an outlet 59 configured to eject a thoroughly mixed solution. Spray tip assembly 50 may be composed of silicone or other suitable biocompatible material.

In one embodiment, spray tip assembly 50 is composed of a silicone elastomer, for example, TUFEL® II 94706, a silicone rubber compound and LIM®6071, a liquid silicone rubber, available from Momentive Performance Materials, Waterford, N.Y. Through testing, it has been found that a spray tip assembly 50 composed of silicone having a 70 durometer, is capable of unclogging itself during operation. It is envisioned that other silicones of varying durometers may also be effective at clearing or unclogging itself. The flexible nature of silicone permits spray tip assembly 50 to flex under the increased pressure experienced during a clog of spray tip assembly 50. The flexion of spray tip assembly 50 dislodges any clog that may form therein. Additionally, the non-wetting surface characteristic (hydrophobicity) of silicone may assist in preventing the clogging of spray tip assembly 50. The ability of spray tip assembly 50 to unclog itself during operations permits the continuous use of applicator assembly 10 without the need to repeatedly change spray tip assembly 50. In this manner, the length of the procedure may be reduced and the expense and inconvenience of using multiple spray tip assemblies is eliminated.

Still referring to FIGS. 3-6, spray tip assembly 50 includes a first chamber 54, an intermediate chamber 56 and a final chamber 58. First chamber 54 defines a substantially cylindrical cavity for receiving distal end 30b of elongated shaft 30. As will be discussed in further detail below, first chamber 54 is configured such that distal end 30b of elongated shaft 30 is received flush against insert 40. It is envisioned, however, that first chamber 54 may be configured such that distal end 30b of elongated shaft 30 is proximally spaced from insert 40. Intermediate chamber 56 defines a substantially cylindrical cavity configured to receive insert 40. Intermediate chamber 56 includes ribs or spacers 56a for maintaining insert 40 (shown in phantom in FIG. 6) centered within intermediate chamber 56. Insert 40 includes a solid, substantially cylindrical member positioned within intermediate chamber 56 to force the first and second components to flow around insert 40 in the space created by ribs 56a. It is envisioned that insert 40 may be sized to extend proximally from intermediate chamber 56 into first chamber 54 to ensure that insert 40 is received flush against distal end 30b of elongated shaft 30.

Figure 4:
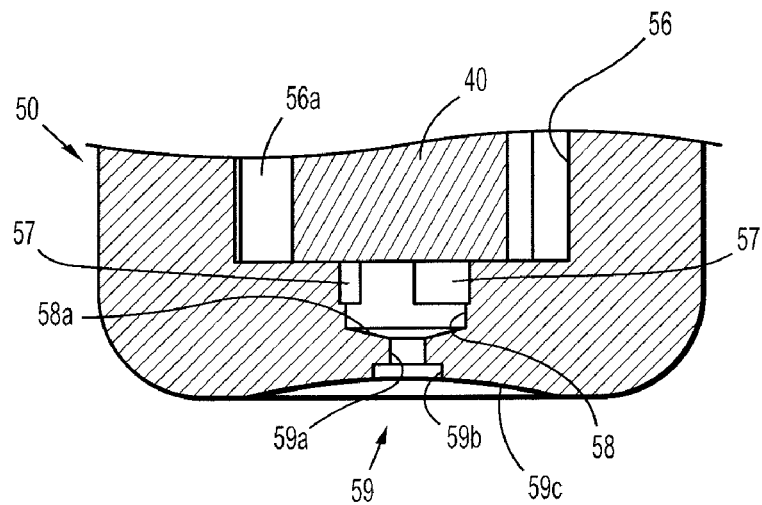
FIG. 4 is an enlarged cross-sectional view of the distal end of the spray tip assembly of FIG. 3.
Figure 5:
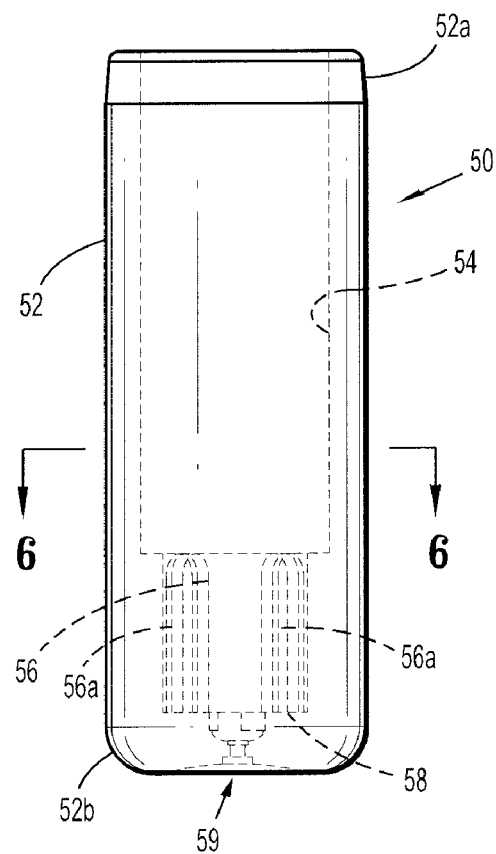
FIG. 5 is a side view of the spray tip assembly of FIGS. 3 and 4 with internal structure shown in phantom.
Figure 6:
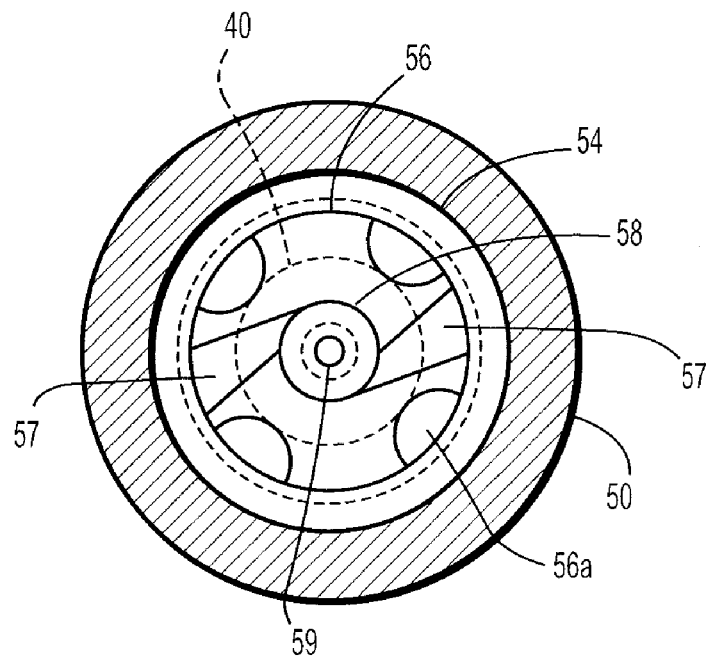
FIG. 6 is a cross-sectional view of the spray tip assembly of FIG. 5 taken along line 6-6.
Figure 6A:
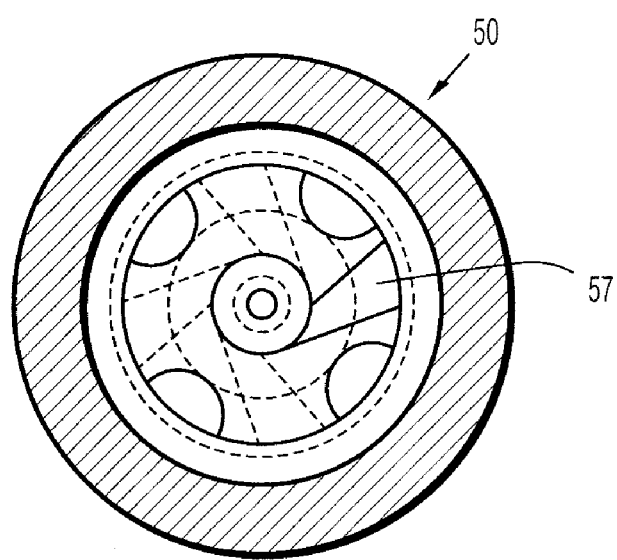
FIG. 6A is a cross-sectional view of an alternate embodiment of the spray tip of FIG. 6.

With reference still to FIGS. 3-6, final chamber 58 defines a substantially cylindrical cavity having a tapered distal portion 58a. Spray tip assembly 50 includes slots 57 formed therein fluidly communicating intermediate chamber 56 and final chamber 58. Slots 57 define opposed openings angling outwardly from final chamber 58 between a line tangent to final chamber 58 and about twenty degrees)(20°) counterclockwise from the tangent line. As will be discussed in further detail below, slots 57 direct the partially mixed first and second components from within intermediate chamber 56 into final chamber 58. Although shown as a pair of opposed openings, it is envisioned that spray tip assembly 50 may include only a single slot 57 (FIG. 6A), or may alternatively include three or more slots 57 (shown in phantom, FIG. 6A). Outlet 59 is configured to atomize the thoroughly mixed solution into a generally cone-shaped spray. As shown in FIG. 4, from proximal to distal, outlet 59 includes a first cylindrical portion 59a, a second cylindrical portion 59b, and a recessed portion 59c. It is envisioned, however, that outlet 59 may be formed without second cylindrical portion 59b.

The operation of applicator assembly 10 will now be described as relates to the figures. Prior to use, insert 40 is received within intermediate chamber 56 of spray tip assembly 50. As discussed above, insert 40 is positioned such that fluid passing through intermediate chamber 56 is forced around insert 40 in the space created between ribs 56a. Spray tip assembly 50 is selectively received on distal end 30b of elongated shaft 30. As discussed above, manifold 20 may be integrally formed with elongated shaft 30, or instead it may be necessary to secure elongated shaft 30 to manifold 20 manually prior to use, making sure that first and second component channels 23, 25 are aligned with first and second component lumens 33, 35. First and second sources of component (not shown) are next connected to first and second proximal extensions 22, 24, respectively. Once secured to manifold 20, first and second sources of component may be activated, e.g., depression of syringe plungers (not shown), to initiate the flow of first and second components within first and second component channels 23, 25, respectively. The first and second components flow through first and second component channels 23, 25, through first and second component lumen 33, 35, respectively, and into spray tip assembly 50.

The first and second components flowing from first and second component lumens 33, 35 encounter insert 40 retained with intermediate chamber 56. First and second component lumens 33, 35 are spaced such that the first and second components may flow around insert 40 in the space created between ribs 56a and insert 40. The first and second components are then forced into slots 57 where they are directed radially inward toward final chamber 58. The flow of the mixture through slots 57 imparts a swirling motion to the mixture as the mixture enters final chamber 58. Thereafter, the thoroughly mixed solution is atomized as it is ejected through outlet 59 in a cone-shaped spray.

Figure 7:
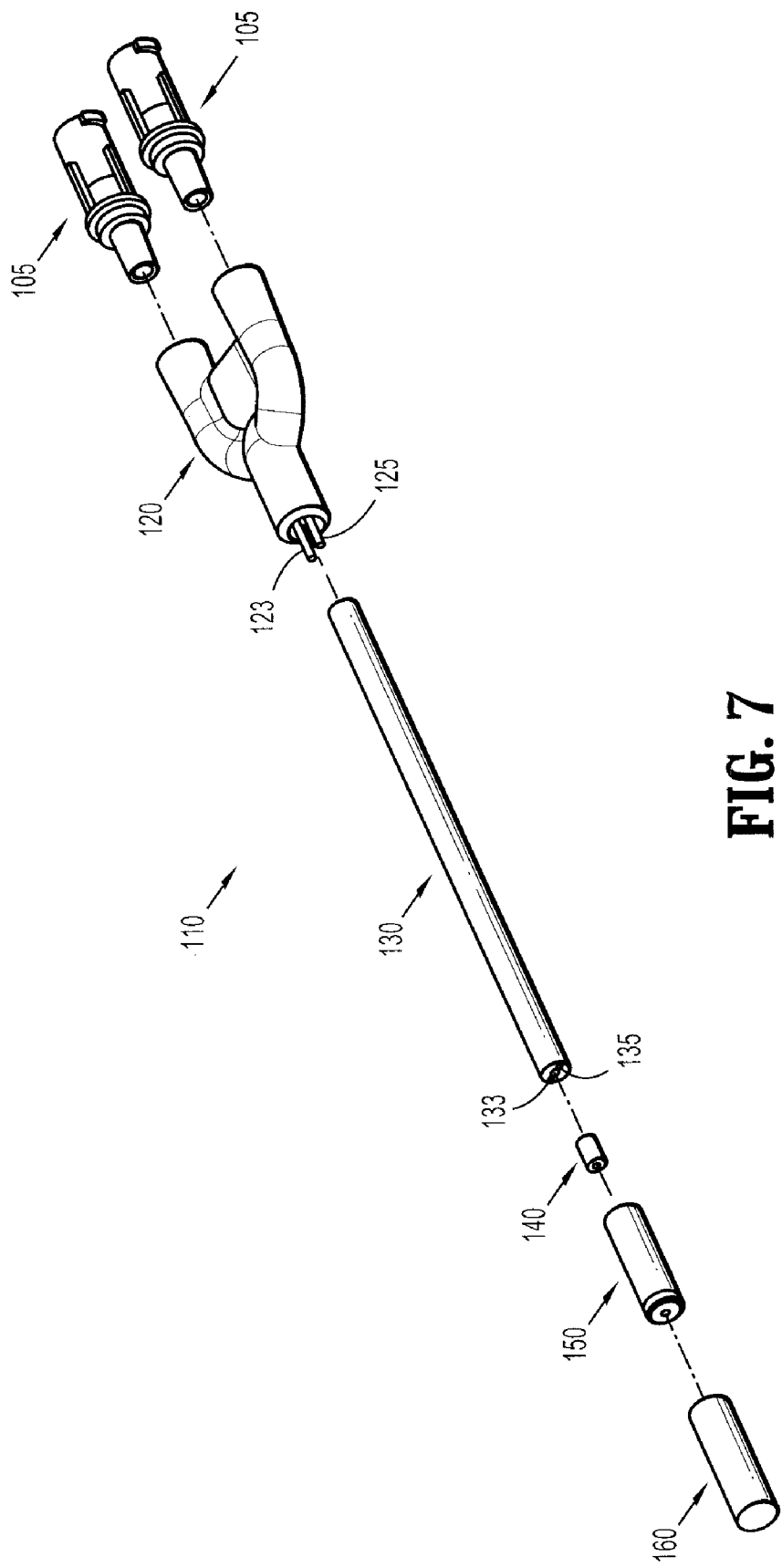
FIG. 7 is an exploded perspective view of an applicator assembly according to another embodiment of the present disclosure.

Turning to FIGS. 7-11, an alternate embodiment of the present disclosure is shown generally as applicator assembly 110. Applicator assembly 110 is substantially similar to applicator assembly 10, and will therefore only be described as relates to the differences therebetween. With reference initially to FIGS. 7 and 8, applicator assembly 110 includes a manifold or base 120 configured to receive a pair of check valves 105, an elongated shaft 130 extending from manifold 120, and a spray tip assembly 150 positioned on a distal end of elongated shaft 130. An insert 140 is received within spray tip assembly 150 and a shrink tube 160 is received about spray tip assembly 150.

Referring to FIG. 7, first and second component channels 123, 125 extend from a distal end of manifold 120. First and second component channels 123, 125 are configured to fluidly communicate with first and second component lumen 133, 135 extending through elongated shaft 130. This configuration permits for a more secure fluid seal between manifold 120 and elongated shaft 130.

Figure 10:
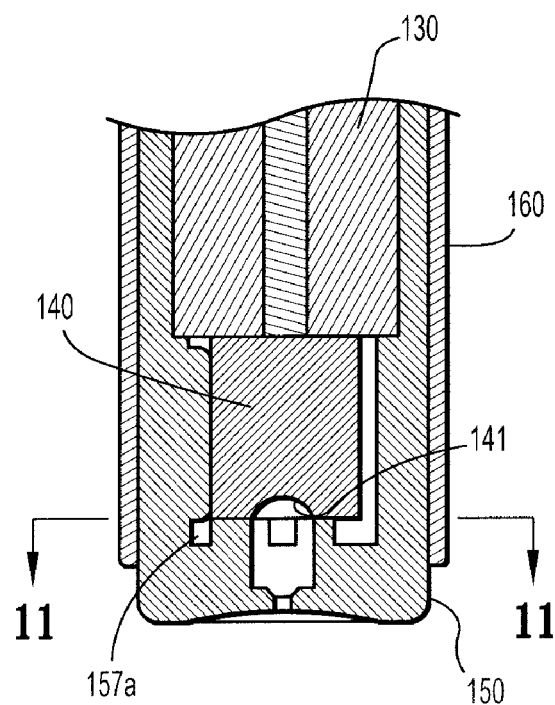
FIG. 10 is an enlarged sectional view of section 10 of FIG. 9.

With reference now to FIGS. 9 and 10, insert 140 is substantially similar to insert 40, including a substantially cylindrical member configured to be received within spray tip assembly 150. As shown, insert 140 includes hemispherical recess 141 on a first end thereof, however, it is envisioned that for ease of manufacture and assembly, hemispherical recess 141 may be formed on both ends thereof. Recess 141 is configured to create turbulence in the flow of the first and second components prior to the mixture being ejected through outlet 59.

Still referring to FIGS. 9 and 10, shrink tube 160 is received about spray tip assembly 150 to prevent the excess radial expansion/flexion of spray tip assembly 150 during operation. Shrink tube 160 may also assist in securing spray tip assembly 150 to elongated shaft 130. Shrink tube 160 may be formed of Teflon® or other suitable material.

Figure 11:
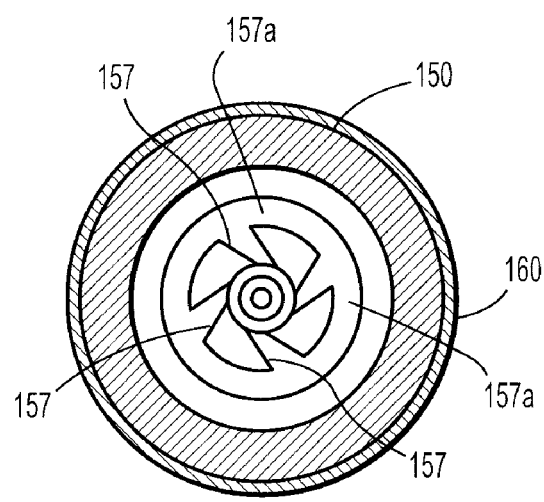
FIG. 11 is a cross-sectional view of the spray tip assembly of FIG. 9 taken along line 11-11 of FIG. 10.
Figure 12:
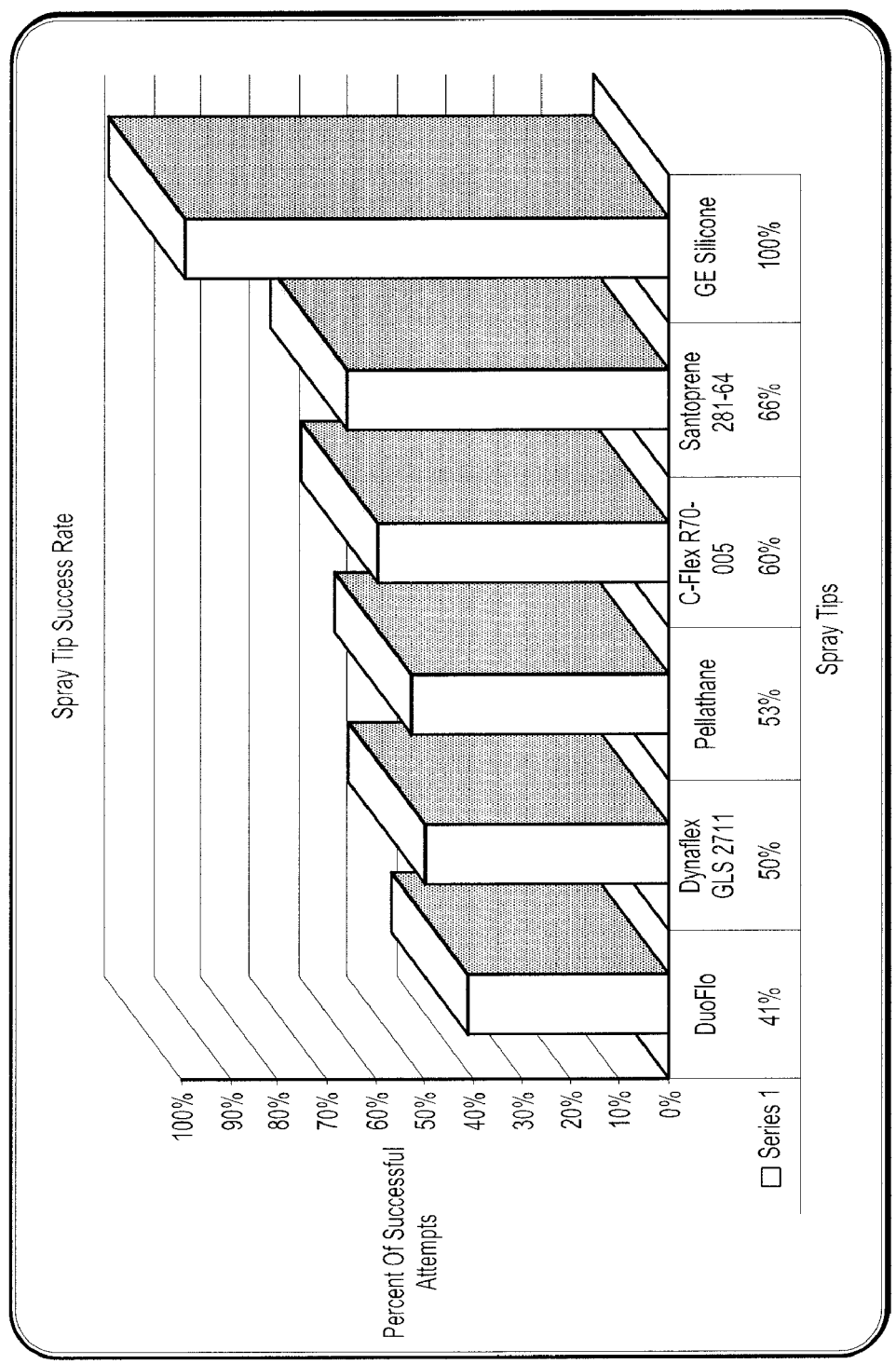
FIG. 12 is a chart showing the results of a study conducted to determine the effectiveness of spray tip assemblies comprised of various materials.

With reference now to FIG. 11, spray tip assembly 150 is substantially similar to spray tip assembly 50, described hereinabove, including radially extending slots 157. A gutter or annular recess 157a is formed about slots 157. Gutter 157a is configured to direct the partially mixed first and second components into slots 157.

With reference now to FIGS. 12-14B, during intermittent use of spray tip assembly 150, outlet 159 of spray tip assembly 150 may become clogged or obstructed as the adhesive retained therein begins to polymerize or gel. A study was conducted comparing the ability of spray tip assemblies of various materials to continue to properly functioning, i.e., continue spraying or unclog itself and continue spraying, after momentarily stopping the spray. The materials tested included C-Flex R70-005 (30 Durometer), Dynaflex GLS 2711 (43 Durometer), Santaprene 281-64 (60 Durometer), Pellathane (90 Durometer) and GE Silicon (70 Durometer). The results of the study show that the spray tip assembly composed of silicone was able to repeatedly unclog itself of any obstruction and continue spraying operation 100% of the time. See, Table 1 below and FIG. 12.

TABLE 1

| Spray Tip Material | Spray Attempts/ Success | Success Rate (%) |
| --- | --- | --- |
| DuoFlo Spray Tip/Thermoplastic | 39/16 | 41% |
| Dynaflex GLS 2711 | 12/6 | 50% |
| Pellathane | 15/8 | 53% |
| C-Flex R70-005 | 15/9 | 60% |
| Santoprene 281-64 | 15/10 | 66% |
| GE Silicone | 15/15 | 100% |

Figure 13A:
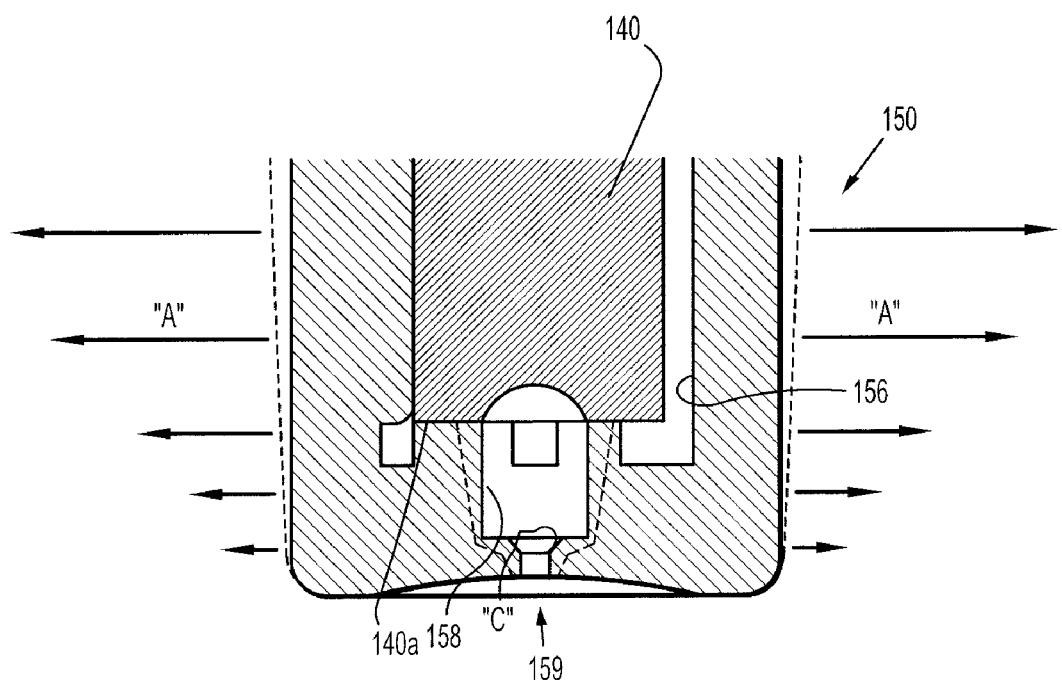
FIG. 13A is a cross-sectional view of the distal end of the spray tip assembly of FIG. 7, in a first or unexpanded and/or unflexed condition.
Figure 13B:
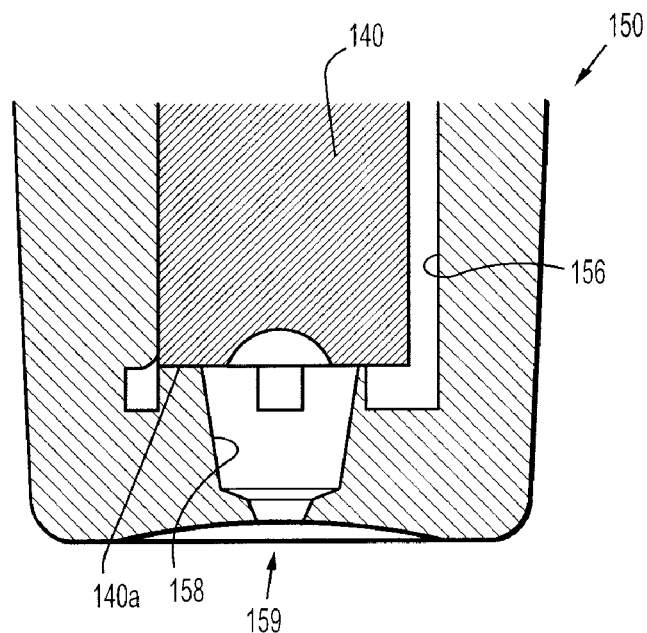
FIG. 13B is a cross-sectional view of the distal end of the spray tip assembly of FIG. 12A, in a radially expanded and/or flexed condition.

With reference to FIGS. 13A and 13B, during operation of spray tip assembly 150, momentary stoppages in spraying may result in the formation of a clog or obstruction "C" that may obstruct outlet 159. The presence of clog "C" in outlet 159 causes at least a partial failure of spray tip assembly 150 to emit a spray, and in many instances, clog "C" completely obstructs the flow through outlet 159. Whether partially or completely blocking outlet 159, clog "C" creates a pressure build-up within spray tip assembly 150. As shown, the pressure build-up created by clog "C" causes spray tip assembly 159 to expand and/or flex radially outward, as depicted by arrows "A". Used herein, expansion refers to stretching of the material while flexion refers to the deformation of the material. Radial expansion and/or flexion of spray tip assembly 150 changes the configuration of outlet 159.

As shown, radial expansion and/or flexion of spray tip assembly 150 causes outlet 159 to increase in diameter along at least a portion thereof. Depending on the degree of radial expansion and/or flexion, final chamber 158 of spray tip assembly 150 may also increase in diameter along at least a portion thererof. The increase in the diameter of outlet 159 permits clog "C" to pass through outlet 159. Once outlet 159 has been cleared of clog "C", the pressure build-up within spray tip assembly 150 dissipates and outlet 159 returns to its original, unexpanded/unflexed configuration. In this manner, spray tip assembly 150 is capable of self-clearing clog "C", self-clearing meaning being able to clear outlet 159 of clog "C" without additional outside influence. Although shown as uniform or symmetric radial expansion/flexion, it is appreciated that the configuration of spray tip assembly 150 may permit asymmetric expansion and/or flexion of spray tip assembly 150. In this manner, outlet 159 may experience asymmetric expansion/flexion, e.g., elongation.

Figure 14A:
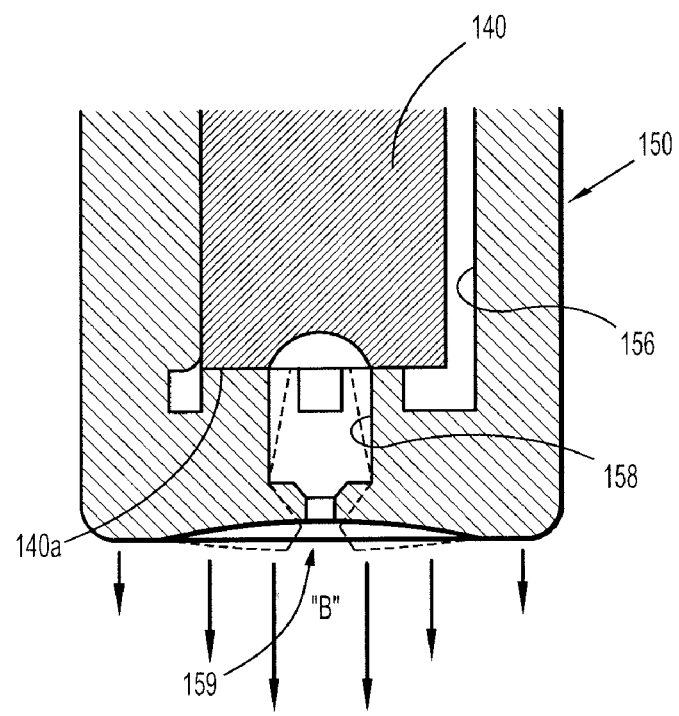
FIG. 14A is a cross-sectional view of the distal end of the spray tip assembly of FIG. 7, in a first or unexpanded and/or unflexed condition.
Figure 14B:
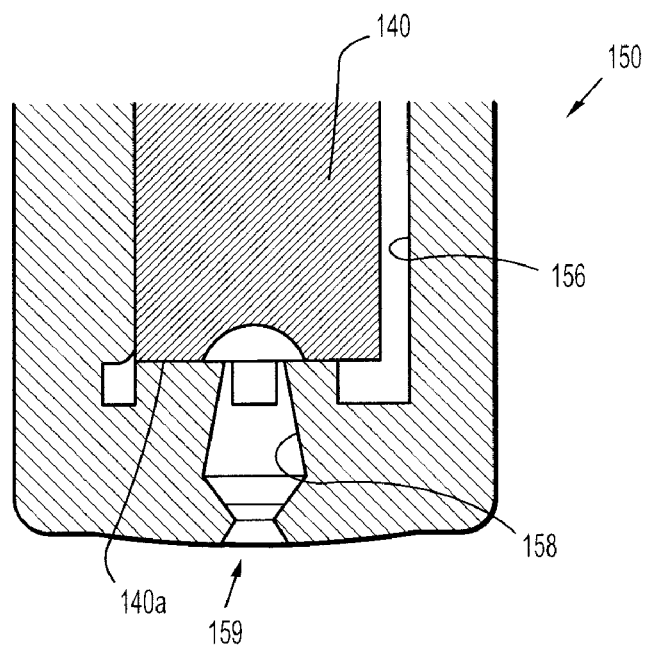
FIG. 14B is a cross-sectional view of the distal end of the spray tip assembly of FIG. 13A, in a longitudinally expanded and/or flexed condition.

Turning now to FIGS. 14A and 14B, the pressure build-up created by clog "C" within spray tip assembly 150 may additionally, or instead, cause spray tip assembly 150 to expand and/or flex in a distal or longitudinal direction, as indicated by arrows "B". Longitudinal expansion and/or flexion of spray tip assembly 150 causes a change in the configuration of outlet 159 (shown in phantom). As shown, longitudinal expansion and/or flexion of spray tip assembly 150 causes outlet 159 to increase in diameter along at least a portion thereof. Depending on the degree of radial expansion and/or flexion, final chamber 158 of spray tip assembly 150 may also increase or decrease in diameter along at least a portion thereof.

Although not shown, intermediate chamber 156 of spray tip assembly 50 may undergo a change in configuration during radial and/or longitudinal expansion/flexion of spray tip assembly 150. During the period of expansion and/or flexion, as clog "C" is cleared from outlet 159, the force of the first and second components against insert 140 maintain distal end 140a of insert 140 flush against a distal end of intermediate chamber 156, thereby ensuring the first and second components are properly directed into final chamber 158.

A second study was conducted to compare the characteristics of variously configured spray tip assemblies 150 with known spray tip assemblies (not shown). Results of the study show that a spray tip assembly 150 including a Teflon® heat shrink tube 160 (FIG. 7) received thereabout improved the start/stop function of spray tip assembly 150. Furthermore, it was found that placing a small space, 1-2 mm, between distal end 130b of elongated shaft 130 and insert 140 demonstrated no improvement in spray performance.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A spray tip assembly comprising:
   an elongated body defining a longitudinal axis;
   a distal end including an outlet formed about the longitudinal axis of the elongated body and having a substantially circular cross-section, the distal end defining at least a first configuration during an at rest first condition and at least a second configuration during a second condition, wherein the outlet is open in both the first and second configurations; and
   a mixing portion configured for mixing at least a first component and a second component.

2. The spray tip assembly of claim 1, wherein the distal end is configured to flex such that the outlet changes from the first configuration to the second configuration.

3. The spray tip assembly of claim 1, wherein the distal end is configured to expand such that the outlet changes from the first configuration to the second configuration.

4. The spray tip assembly of claim 1, further including a proximal end configured for operable engagement with a dispensing assembly.

5. The spray tip assembly of claim 1, wherein the distal end comprises a material that permits at least one of flexion and expansion.

6. The spray tip assembly of claim 1, wherein at least a portion of the distal end comprises silicone.

7. The spray tip assembly of claim 1, wherein the outlet defines the first configuration during normal operation and the second configuration when the outlet is at least partially obstructed.

8. The spray tip assembly of claim 1, wherein the distal end at least one of flexes and expands radially to change from the first configuration to the second configuration.

9. The spray tip assembly of claim 1, wherein the distal end at least one of flexes and expands distally to change from the first configuration to the second configuration.

10. The spray tip assembly of claim 1, wherein the distal end at least one of flexes and expands both radially and distally to change from the first configuration to the second configuration.

11. The spray tip assembly of claim 1, wherein the outlet defines an opening have a first diameter in the first configuration and a larger diameter in the second configuration.

12. A self-clearing applicator comprising:
    an elongated body defining a longitudinal axis;
    a spray tip assembly operably connected to a distal end of the elongated body and having a distal end including an outlet defining an axis that is coaxial with the longitudinal axis of the elongated body, the outlet defining at least a first open configuration at rest and during normal operation and at least a second open configuration when the outlet is at least partially obstructed, wherein a distal surface of the distal end defines a recess about the outlet; and
    a mixing portion configured for mixing at least a first component and a second component.

13. A self-clearing applicator comprising:
    a spray tip assembly including an outlet having an open configuration at rest, wherein the outlet includes a first cylindrical portion, a second cylindrical portion and a recessed portion, each of the first cylindrical portion, the second cylindrical portion and the recessed portion being deformable to permit clearing of an obstruction from within the outlet; and
    a mixing portion configured for mixing at least a first component and a second component.

14. A self-clearing applicator comprising:
    a spray tip assembly including a mixing portion and defining an outlet, the spray tip assembly capable of undergoing a change in cross-sectional geometry from a first configuration, at rest and during normal use, wherein the outlet includes a first diameter, to a second configuration wherein the outlet includes a second diameter to clear an obstruction from the outlet, the mixing portion includes at least a first radially inward extending slot for directing a partially mixed solution towards the outlet.

15. The self-clearing applicator of claim 14, wherein the first and second diameters are different.

16. The spray tip assembly of claim 1, wherein a distal surface of the distal end defines a recess about the outlet.

17. The self-clearing applicator of claim 14, wherein a distal surface of the spray tip assembly defines a recess about the outlet.

* * * * *